United States Patent
Yasumoto

(12) United States Patent (10) Patent No.: US 6,634,216 B1
Yasumoto (45) Date of Patent: Oct. 21, 2003

(54) INSPECTION METHOD FOR SEALED PACKAGE

(75) Inventor: Kenji Yasumoto, Toyonaka (JP)

(73) Assignee: Joven Denki Kabushiki Kaisha, Osaka (JP)

(*) Notice: Subject to any disclaimer, the term of this patent is extended or adjusted under 35 U.S.C. 154(b) by 0 days.

(21) Appl. No.: 09/743,332

(22) PCT Filed: Jun. 25, 1999

(86) PCT No.: PCT/JP99/03447

§ 371 (c)(1), (2), (4) Date: Jan. 5, 2001

(87) PCT Pub. No.: WO00/03239

PCT Pub. Date: Jan. 20, 2000

(30) Foreign Application Priority Data

Jul. 10, 1998 (JP) ............................................. 10-211868
Jun. 9, 1999 (JP) ............................................. 11-162937

(51) Int. Cl.$^7$ ......................... G01R 31/12; G01N 27/00
(52) U.S. Cl. .............................. 73/49.3; 73/52; 324/557; 324/558
(58) Field of Search ..................... 73/49.3, 52; 324/557, 324/558, 536

(56) References Cited

U.S. PATENT DOCUMENTS

| 4,125,805 A | * 11/1978 | Nagamatsu et al. | 324/558 |
| 4,243,932 A | * 1/1981 | Kakumoto et al. | 324/557 |
| 4,914,395 A | * 4/1990 | Hamada | 324/557 |
| 5,378,991 A | * 1/1995 | Anderson et al. | 324/450 |
| 5,760,295 A | * 6/1998 | Yasumoto | 73/49.3 |
| 5,850,144 A | * 12/1998 | Howells et al. | 324/559 |
| 6,009,744 A | * 1/2000 | Kovalchick et al. | 324/536 |
| 6,288,554 B1 | * 9/2001 | Yasumoto | 324/558 |

FOREIGN PATENT DOCUMENTS

| JP | S59-125035 | 7/1984 | | |
| JP | 63101728 A | * 5/1988 | ............... | 73/52 |
| JP | 03150440 A | * 6/1991 | ............... | 73/52 |
| JP | H9-222420 | 8/1997 | | |

* cited by examiner

Primary Examiner—Edward Lefkowitz
Assistant Examiner—Michael Cygan
(74) Attorney, Agent, or Firm—Koda & Androlia

(57) ABSTRACT

The invention provides an efficient inspection method for inspecting a hermetically sealed package for pinholes, in which when a hermetically sealed package whose contents such as electrically conductive fluid or food are covered with an electrically insulating film is inspected for pinholes by using a high voltage, the inspection can be achieved with an extremely simple procedure while fully preventing occurrence of misoperations due to the atmosphere such as humidity during the inspection.

In a hermetically sealed package in which contents 1 such as electrically conductive fluid are covered with an electrically insulating film 2, an electrical conductor 4 derived from a voltage output terminal of a DC high voltage power supply 6 is put into contact with or proximity to a side face portion 3$_1$ of the hermetically sealed package, by which the contents 1 in the hermetically sealed package 3 are electrified. Next, a lead wire 8 is connected to a connecting terminal 5$a$ of an electrode 5 put into close contact with or opposed proximity to an inspection-object portion 3$a$ of the package 3 where pinholes are most likely to occur, and the lead wire 8 is grounded. Then, a discharge current derived from the inspection-object portion 3$a$ that flows only when a pinhole is present is detected by a discharge current detector 7, by which the presence or absence of a pinhole is detected depending on the presence or absence of the discharge current. In this procedure, the inspection can be made by placing the package on a support electrode derived from an AC high voltage power supply and electrifying the contents.

11 Claims, 4 Drawing Sheets

(A)

(B)

INSPECTION METHOD FOR SEALED PACKAGE

TECHNICAL FIELD

The present invention relates to a method for inspecting completely hermetically sealed packages, such as food and medical consumption articles, for any pinholes.

BACKGROUND ART

Today, hermetically sealed packaging is used in a variety of commodities including food and medical consumption articles such as physiological saline to keep their contents in a sterilized state. In the case of food, the presence of pinholes would cause the contents of the package to contact the air, resulting in deterioration or rot. Also, in the case of medical consumption articles, for example, transfusion bottles, the presence of pinholes would cause contamination or deterioration. Thus, the pinhole inspection for these hermetically sealed packages is of great importance. Conventionally, this pinhole inspection would be carried out in the following method. That is, because a hermetically sealed package does not allow an electrode to be penetrated thereinto, for example in the case of food, a metal pin is stuck into a completed package and taken as one electrode so as to serve as an opposed electrode to an external electrode set in contact with the package. In this state, with a high voltage applied between the two electrodes, the hermetically sealed package is inspected for pinholes, and after the inspection, any pinholes are hermetically sealed in a different process. However, this inspection method has had a drawback that the inspection process would be complicated, requiring a subsequent process of closing the pinholes. A method for pinhole inspection which solves this drawback and which allows a pinhole inspection to be done without damaging the completed hermetically sealed package has been disclosed in, for example, Japanese Patent Publication SHO 50-6998. In this method, a food hermetically sealed by a package made from an electrically insulating film is sandwiched between a pair of electrodes, and a voltage is applied between both electrodes so as to give a large difference between capacitances that are formed between the individual electrodes and the food, respectively. Then, a current which is generated by a spark between one of the electrodes and the food is detected, by which any pinhole is detected.

When the presence or absence of any pinhole is detected by detecting a short-time current generated by a spark as described above, it would be the actual case in terms of practical work that the presence or absence of pin holes is detected by a change (magnitude) of the detected current. In this case, applying a voltage between the two electrodes that sandwich the hermetically sealed package would cause a leakage current or charging current to necessarily flow regardless of the presence or absence of pinholes. This phenomenon is more likely to occur particularly with higher voltage, and is also affected by weather such as humidity and temperature of the periphery of the inspection object, which forms the atmosphere during the inspection, where the leakage current becomes larger under the conditions of rain or high humidity. Further, there may arise an error to the current at the detection point due to some influence of floating fine dusts or the like. As a result, the decision as to the presence or absence of pinholes by the magnitude of the short-time current could not be free from misoperations such as a decision of the presence of a pinhole notwithstanding the absence of any pinhole.

The present applicant has previously proposed an inspection method in Japanese Patent Applications HEI 8-53816 and HEI 10-158569. In this method, the hermetically sealed package is placed on a support electrode of a specified configuration, such as a grounded electrode plate, with side face portion of the hermetically sealed package put into contact with the support electrode, and a DC high voltage is applied between the support electrode and an electrode put into close contact with or opposed proximity to an inspection-object end portion of the hermetically sealed package so that the contents of the hermetically sealed package are electrically charged. Then, with the support electrode either released from grounding or kept grounded, the electrode put into contact with the inspection-object end portion is grounded, where a discharge current from the inspection-object end portion is detected, by which any pinhole of the hermetically sealed package is detected.

This method has made it possible to efficiently inspect a hermetically sealed package for the presence or absence of any pinholes by an inspection of the inspection-object end portion at a site where pinholes are most likely to occur while misoperations are fully prevented during the inspection of pinholes of the hermetically sealed package. However, the method has still required a sequence of inspection procedure.

The present invention has been accomplished in view of these and other problems. An object of the present invention is therefore to provide an efficient method for inspecting a hermetically sealed package which method allows the inspection to be achieved with further simpler procedure and which is fully prevented from occurrences of misoperations due to the atmosphere during the inspection.

For this method, the hermetically sealed package to be inspected can be exemplified, in the field of food, principally by cylindrical-shaped packages such as sausage hermetically sealed and packaged in unit pieces, and besides retort foods packed in a flat bag made of plastic film. In the field of medical consumption articles, the hermetically sealed package can be exemplified by blood preparations such as transfusion blood and blood plasmas contained in a plastic bag in addition to transfusion agents such as physiological saline or Ringer's solution contained in a transfusion bottle also made of plastic as the inspection object for prevention of contamination and deterioration of the contents due to contact with outside air via pinholes. Furthermore, hermetically sealed packages in which a particle or powder conductive material such as cooked rice or solid-matter iron powder is hermetically sealed in a plastic bag also can be an object of inspection as well.

DISCLOSURE OF INVENTION

In order to achieve the above object, the present invention provides a method for inspecting any pinholes of a hermetically sealed package 3 in which contents 1 such as electrically conductive fluid or powder or food are covered with an electrically insulating film 2, the method comprising steps of: putting a single electrode 4 derived from a voltage output terminal of a high voltage power supply 6 into contact with or proximity to a side face portion 3, of the hermetically sealed package 3 so that the contents 1 in the hermetically sealed package 3 are electrified; then grounding an electrode 5 put into close contact with or opposed proximity to an inspection-object portion 3a of the hermetically sealed package 3; and detecting a discharge current from the inspection-object portion 3a to thereby detect any pinhole of the hermetically sealed package 3. In this method, the electrode 5 may be implemented by electrically conductive liquid or electrically conductive gel.

With such a method, when the single electrode 4 derived from the voltage output terminal of the high voltage power supply 6 is put into contact with or proximity to the side face portion $3_1$ of the hermetically sealed package 3, the electrically conductive contents 1 within the hermetically sealed package 3 are electrified by a negative or positive potential of the high voltage (0.6 kV–30 kV) applied to the electrode 4, so that negative (−) ions or positive (+) ions are generated.

Next, upon the grouping of the electrode 5 put into close contact with or opposed proximity to the inspection-target portion 3a of the hermetically sealed package 3, in the case where a pinhole is present at the inspection-object end portion 3a, if negative (−) ions are generated in the contents 1, the negative (−) ions gather to the pinhole and negative (−) electrons within the negative (−) ions collectively flow through the pinhole toward the ground (earth), so that the negative charges are lost, thus resulting in discharge. On the other hand, if positive (+) ions are generated in the contents 1, the positive (+) ions gather to the pinhole and positive charges are lost by negative (−) electrons flowing from the ground side through the pinhole, thus resulting in discharge. Without any pinhole, negative (−) electrons in the negative (−) ions do not flow toward the ground, and the negative (−) ions do not flow from the ground side against the positive (+) ions, go the charges of the contents are not discharged.

Therefore, any pinhole at the inspection-object portion can be detected by detecting the resulting discharge current, where the discharge current could not be detected without the presence of any pinhole at the inspection-object portion 3a. Also, without any pinhole, although the contents 1 are electrified, the electricity is discharged little by little like static electricity so that the electrification dissipates.

In this detection, any pinhole can be detected without errors, irrespective of the atmosphere during the inspection, where the decision is made not by any change (magnitude) of the charging current but by the presence or absence of a discharge current due to the presence or absence of a pinhole at the inspection-object portion 3a (where pinholes are most likely to occur).

Furthermore, as the electrode to be used for electrification of the contents, a single electrode derived from the high voltage output side of the high voltage power supply may be used without requiring a pair of electrodes as would be involved in the prior art.

A DC high voltage power supply may properly be used as the high voltage power supply 6. As the electrode 4 derived from the voltage output terminal of this DC high voltage power supply 6, it is effective to use an electrical conductor which can freely be put into contact with or proximity to the side face portion $3_1$ of the hermetically sealed package 3.

An AC high voltage power supply may also be used as the high voltage power supply 6. In this case, it is desirable to use, as the electrode 4 derived from the high voltage output terminal of this AC high voltage power supply 6, a support electrode which allows the hermetically sealed package to be placed thereon with the side face portion $3_1$ of the hermetically sealed package put into contact with the support electrode, so that discharge through any pinhole from electric charges of the contents that are electrified positively (+) and negatively (−) alternately can be detected by a discharge current detecting device.

Use of an AC high voltage power supply as the high voltage power supply is advantageous in that repetitive inspections are enabled, as compared with the use of a DC high voltage power supply. The reason of this is that, when charges with which the contents are electrified are discharged through a pinhole to a number of times with the use of DC current, some contents become less likely to discharge after some times of discharge, but use of AC current is free from such occurrence.

Another advantage is that, after the product inspection, whereas the remaining charges discharge gradually in the case of DC current, the product, which has been repetitively electrified positively (+) and negatively (−) alternately, does not remain electrified in the case of AC current. Moreover, the greatest advantage is that the need for a rectifier device for converting AC current into DC current is eliminated, allowing the product to be offered inexpensively.

Furthermore, as the electrode 5, electrically conductive rubber or electrically conductive plastic formed so that the electrode 5 can be put into close contact with the inspection-object portion 3a may be used. That is, in the case where the inspection-object portion 3a is provided by a die-molding product of mass production, or in other like cases, the inspection-object portion 3a maintains constant or generally constant in shape, so that the electrode 5 can be easily put into close contact with the surface of the inspection-object portion by taking advantage of the elasticity of this electrically conductive rubber or electrically conductive plastic.

BRIEF DESCRIPTION OF DRAWINGS

FIG. 1 is an arrangement diagram of an inspection method of the present invention with a DC high voltage power supply in the case where the hermetically sealed package is a transfusion bottle for physiological saline or the like;

FIG. 2 is an arrangement diagram of an inspection method of the invention with an AC high voltage power supply in the case where the hermetically sealed package is a transfusion bottle for physiological saline or the like;

DESCRIPTION OF THE REFERENCE NUMERALS

Figure 1:
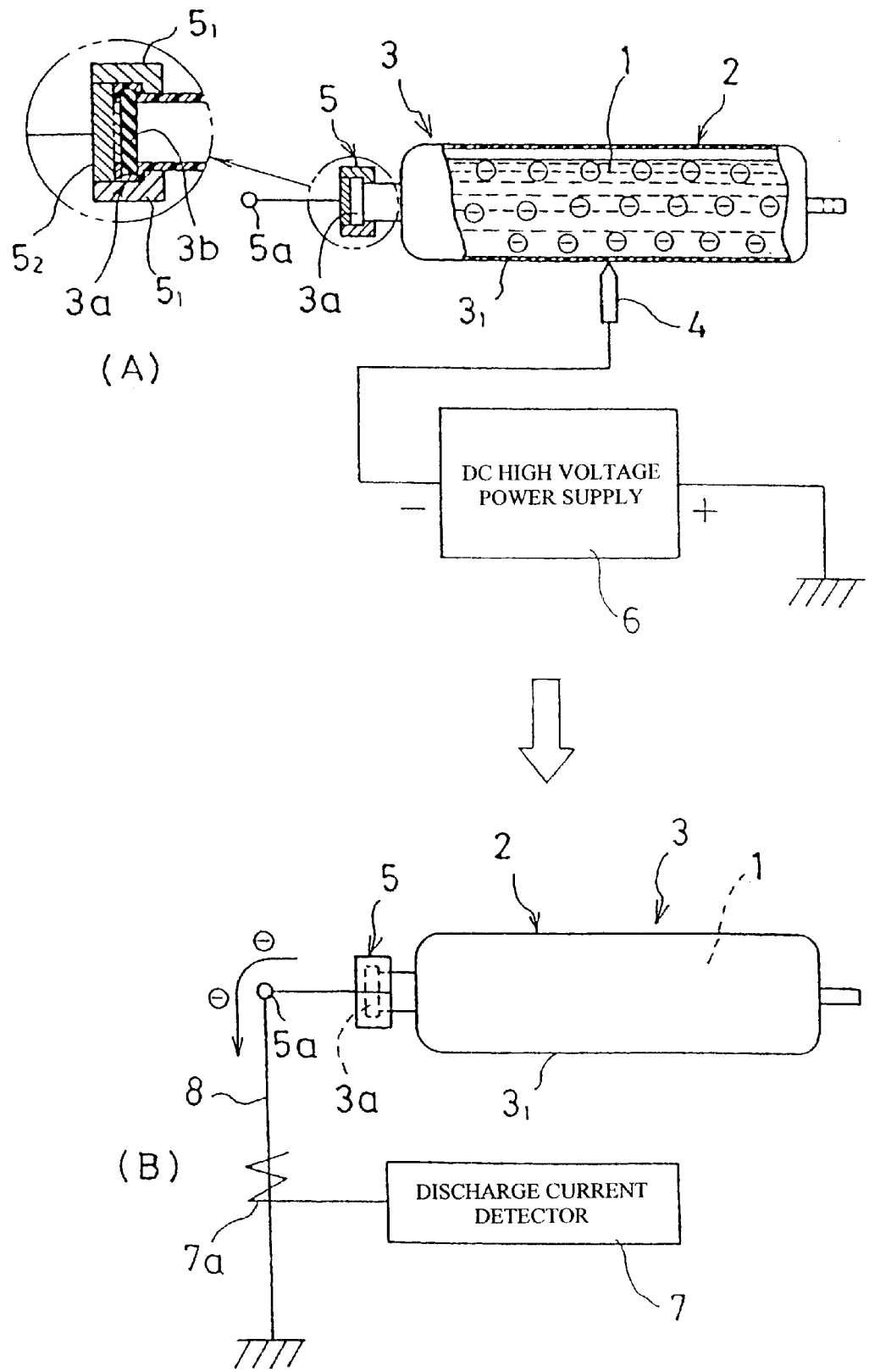

1 . . . contents, 2 . . . electrically insulating film, 3 . . . hermetically sealed package, $3_1$ . . . side face portion of hermetically sealed package, 3a . . . inspection-object portion, 4 . . . electrode (electrical conductor or support electrode), 5 . . . electrode (inspection-object portion side), 6 . . . high voltage power supply (DC high voltage power supply or AC high voltage power supply), 7 . . . discharge current detector

BEST MODE FOR CARRYING OUT THE INVENTION

In the present invention, the electrically insulating film 2 with which the electrically conductive contents 1 of the hermetically sealed package 3 to be inspected are covered may be plastic or plastic film or glass matching the contents.

More specifically, when the contents 1 are fish sausage as an example, a bag made of vinylidene chloride film is used. After minced meat of fish sausage is filled in the beg, the bag is clipped at both ends by aluminum wire and subjected to retort sterilization. Further, even retort foods employing a bag of composite film (laminate film) containing no aluminum foils in their internal layers can be the objective hermetically sealed package to be inspected. In this case, bags of a composite film made of nylon and polypropylene, polyester and polypropylene, or polyester and vinylidene chloride and polypropylene are used. On the other hand, in the case of transfusions such as physiological saline and Ringer's solution, transfusion bottles of a plastic specified for individual cases are used and besides glass containers are also usable.

Furthermore, the contents 1 may also be less electrically conductive distilled water, ultraviolet cutting cosmetics, or fluids of solid matters, such as iron powder or other electrically conductive powder, as the electrically conductive fluid.

For supporting the hermetically sealed package 3 in order that the single electrode 4 is put into contact with or proximity to the side face portion $3_1$ of the hermetically sealed package 3 so as to electrify the contents 1, the support member may be of any shape, such as a planar support member (either plastic or metallic depending on the circumstances of use), a support member whose upper contact surface is planar shaped with many rollers of small diameter located adjacent to one another, or a support member having a circular-arc inner surface so that the cross section of the support member corresponds to the circular sausage or the like. For AC high voltage power supply, the support member may be a metallic, planar-shaped one, or one whose upper contact surface is planar shaped with many rollers of small diameter located adjacent to one another, or one having a circular-arc inner surface, or the like as described above. Also, the electrode 5 to be put into close contact with or opposed proximity to the inspection-object portion 3a may be a metallic one, and further may be ones made of electrically conductive rubber (porous conductive rubber) or electrically conductive plastic formed so that the electrode 5 can be put into close contact with the inspection-object portion 3a. For the detection of a discharge current from the inspection-object portion 3a, a current transformer (CT) of such a type that its detection portion is wound around a lead wire through which the discharge current flows, or a current detector (residual charge detector) connected in series to the lead wire may be used. Furthermore, the discharge current can be measured by inputting to an oscilloscope an output of a current probe through which the lead wire is passed.

EXAMPLE 1

FIG. 1 shows an inspection state with a DC high voltage power supply in the case where the hermetically sealed package 3 is a transfusion bottle for use in instillation in which physiological saline is hermetically sealed.

The transfusion bottle 3 has a body portion formed of a rather thick plastic film 2 with a cross section formed into a rounded 65 mm×90 mm rectangular shape having a height of 240 mm, and a content volume of 1000 milliliters. The inspection-object portion 3a of the hermetically sealed package 3 where pinholes are liable to occur is one formed in such a way that a rubber stopper portion 3b for insertion of an instillation needle is provided airtight at an opening of a stepped end portion having an outer diameter of 28 mm and a thickness of 8 mm while a hanging ring portion is provided on the opposite side. Places in this inspection-object portion 3a where pinholes or gaps equivalent to pinholes are liable to occur are peripheries of the ring-shaped stepped portion at which the rubber stopper portion 3b is held, and the boundary portion between the rubber stopper portion 3b and the opening of the stepped portion at which the rubber stopper portion 3b is held.

In order to inspect the inspection-object portion 3a of this transfusion bottle 3 for pinholes, with the transfusion bottle 3 placed on an arbitrary support base made of, for example, plastic (not shown), first a tip of an electrical conductor 4 serving as an electrode and connected to the negative (−) side of the DC high voltage power supply 6 whose positive (+) side is grounded is put into contact with or proximity to the inspection-object portion 3a of the transfusion bottle 3, so that the contents 1 within the transfusion bottle 3 are electrified by the negative (−) potential of the DC high voltage (0.6 kV–30 kV) applied to the electrical conductor 4. Also, with a view to taking out the discharge current from the inspection-object portion 3a in the presence of a pinhole at the inspection-object portion 3a, the electrode 5 to be put into close contact with the inspection-object portion 3a is composed of a metallic ring portion comprising two-divided portions $5_1$, $5_1$ having a specified cross-sectional shape, and a metallic tablet portion $5_2$ of a specified cross section which is so formed as to be fit into the ring portion in close contact with a front surface of the rubber stopper portion 3b. The electrode 5 is put into use by being brought into close contact with the inspection-object portion 3a from both sides and front side, respectively. The fitting of this electrode 5 to the inspection-object portion 3a may be done either after the electrical conductor 4 has been brought into contact with or proximity to the side face portion $3_1$ of the transfusion bottle 3 or before the electrical conductor 4 is so done.

Once the electrical conductor 4 is put into contact with or proximity (in the case of a high power supply voltage, e.g., 30 kV) to the side face portion $3_1$ of the transfusion bottle 3, infusion solution 1, which is the contents, is electrified via the insulating film of the transfusion bottle 3 with the negative high potential of the electrical conductor 4.

Next, a lead wire 8 is connected to a connecting terminal 5a of the electrode 5 on the inspection-object portion 3a side, and the lead wire 8 is grounded. This lead wire 8 is additionally equipped with a discharge current detector 7 having a current detecting portion 7a surrounding the lead wire 8 purposed for the detection of a current flowing through the lead wire 8. The discharge current detector 7 may be a specified current transformer (CT), whereas a current detector connected in series between the electrode 5 and the ground may also be used for the detection of current. Furthermore, a discharge current can be detected and measured by inputting to an oscilloscope an output of a current probe penetrated through the lead wire 8.

With this arrangement, when a pinhole is present in the inspection-object portion 3a, a discharge current flows through the lead wire 8, allowing the discharge current detector 7 to detect the discharge current. When there are no pinholes, the discharge current detector 7 does not detect any discharge current. In this case, the time for which the discharge current keeps flowing, i.e., the time in which the electric charges having electrified the contents 1 are dissipated is a moment, whereas the current value is extremely high on the order of several amperes to several tens of amperes. Accordingly, by using this current detection output to make a display with some appropriate display means such as a meter, an alarm buzzer or an alarm lamp, the presence or absence of pinholes at the inspection-object portion 3a can be known with ease.

In addition, it can be seen in the figure that the tip of the electrical conductor 4 is brought into contact with the side face portion $3_1$ of the transfusion bottle 3 from below. Otherwise, the tip of the electrical conductor 4 may of course be brought into contact from side horizontally, or from above vertically.

EXAMPLE 2

Figure 2:
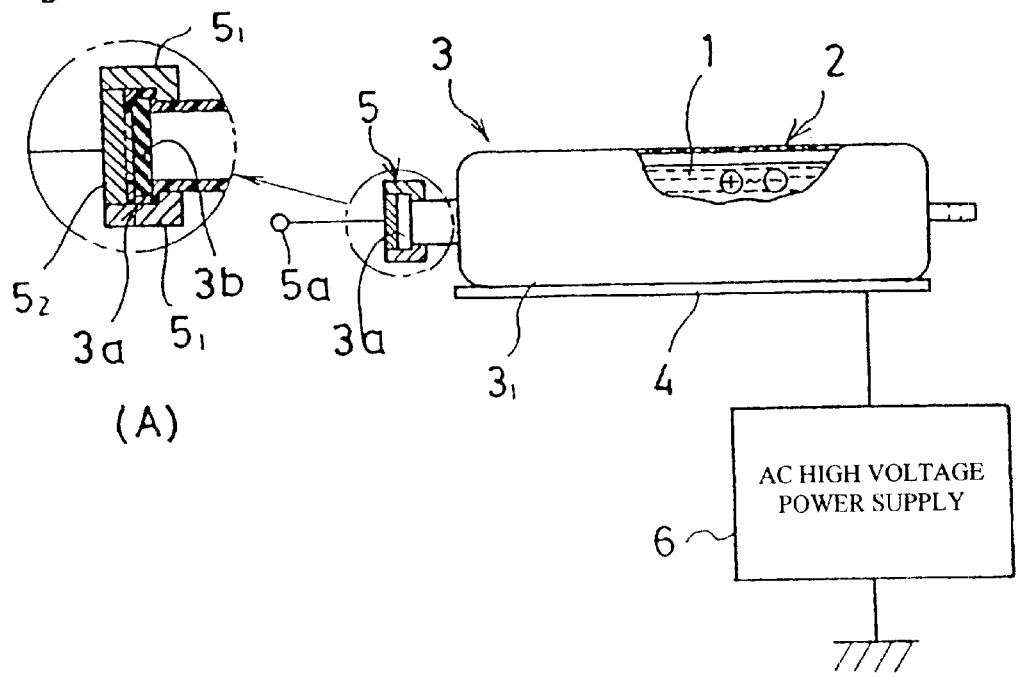
Figure 2:
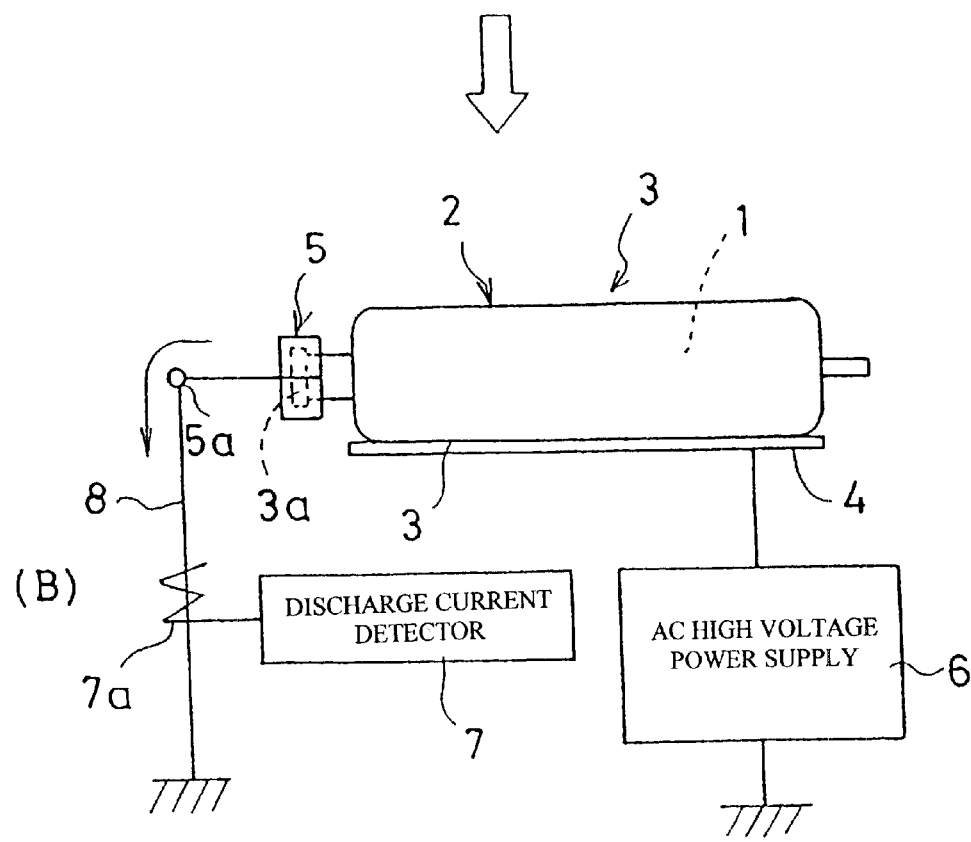

FIG. 2 shows a case where the hermetically sealed package 3 is a transfusion bottle for use in instillation in which physiological saline is hermetically sealed as in Example 1, and where, with a single support electrode for the hermetically sealed package used as the electrode 4 that is to be brought into contact with the side face portion $3_1$ of the hermetically sealed package, the inspection-object portion 3a of the hermetically sealed package 3 is inspected for pinholes by applying an AC high voltage from an AC high voltage power supply 6 to the support electrode 4.

The transfusion bottle 3 is the same as that of Example 1 and so its detailed description is omitted.

The support electrode 4 is implemented by, for example, a flat aluminum plate of specified dimensions that supports the overall side face portion $3_1$ of the transfusion bottle 3. A lower portion of the support electrode 4 is connected via the lead wire to a high-voltage output side terminal of the AC high voltage power supply 6 with output-side one end grounded.

The electrode 5 to be put into close contact with the inspection-object portion 3a is the same as that of Example 1, and used as it is fitted to the inspection-object portion 3a as in Example 1.

When the transfusion bottle 3 for instillation is placed on the support electrode 4, the contents 1 of the transfusion bottle 3 are electrified positively (+) and negatively (−) alternately through the electrically insulating film 2 by the high potential that changes between positive (−) and negative (−) of the AC high voltage (e.g., AC 5 kV) applied to the support electrode 4.

Next, a lead wire 8 is connected to the connecting terminal 5a of the electrode 5 on the inspection-object portion 3a side, and the lead wire 8 is grounded. This lead wire 8 is additionally equipped with a discharge current detector 7 having a current detecting portion 7a surrounding the lead wire 8 purposed for the detection of a discharge current flowing through the lead wire. The discharge current detector 7 may be a specified current transformer (CT) or an oscilloscope like Example 1, whereas a current detector connected in series between the electrode 5 and the ground may also be used for the detection of current.

With this arrangement, in the case where a pinhole is present in the inspection-object portion 3a, a discharge current flows through the lead wire 8 when the contents 1 that have been electrified positively (+) and negatively (−) alternately and that are within the transfusion bottle 3 placed on the support electrode 4 have their charge value reaching a positive (+) or negative (−) high potential, thus allowing the discharge current detector 7 to detect the discharge current. On the other hand, in the case where no pinholes are present, there flows no discharge current so that the discharge current detector 7 does not detect any discharge current. With a pinhole present, because of a high current value of the discharge current, by using this current detection output to make a display with some appropriate display means such as a meter, an alarm buzzer or an alarm lamp, the presence or absence of pinholes at the inspection-object portion 3a can be known with ease, as in Example 1.

In addition, for the pinhole inspection of the hermetically sealed package with an AC high voltage power supply, a discharge current was able to be confirmed as a result of conducting a test at Technology Research Institute of Osaka Prefecture, where with glucose solution containers (including contents) and other specimens for pinhole detection, a 5 kV AC high voltage was applied to the support electrode and the discharge electrode was brought into proximity to the inspection-object portion of the specimen grounded (late in April, 1999).

EXAMPLE 3

Figure 3:
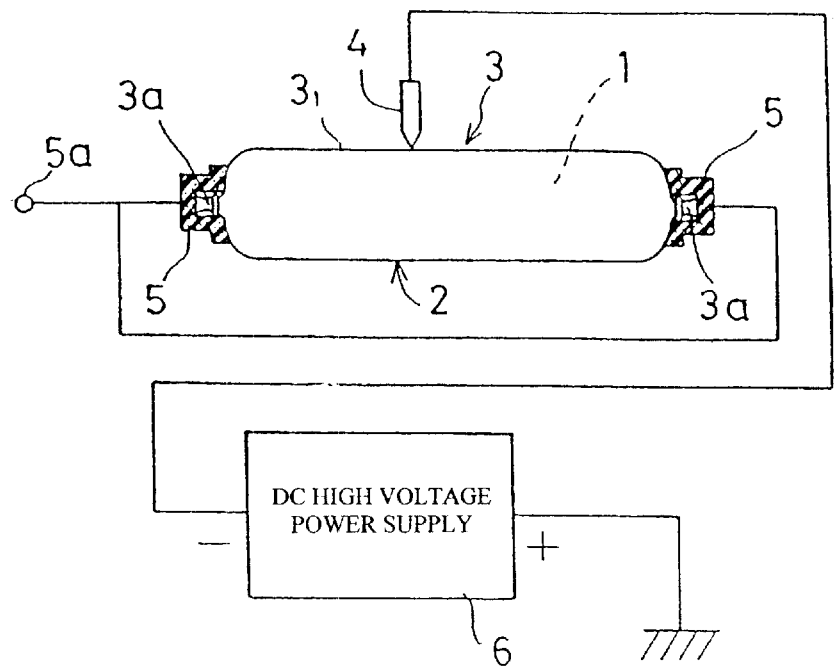
FIG. 3 is an arrangement diagram showing a pre-stage of the inspection method of the invention with a DC high voltage power supply in the case where the hermetically sealed package is a sausage with both ends tightly bound.

FIG. 3 shows a case in which the inspection-object portion 3a of the hermetically sealed package 3 is a tightly binding portion of a bag in which contents 1 are hermetically sealed with an electrically insulating film 2, where the electrical conductor 4 as an electrode derived from the output terminal of the DC high voltage power supply 6 on the negative side is put into contact with the side face portion $3_1$ of the inspection object 3 so that the contents 1 are electrified by a high voltage (0.6 kV–30 kV) of the DC high voltage power supply 6. In this case, pinholes which may occur to the electrically insulating film 2 will be concentrated around this inspection-object portion 3a.

The contents 1 are, for example, fish sausage or the like. As the electrically insulating film 2, a single-substance film of vinylidene chloride is used by virtue of its transparency and superior contractibility and barrier property, and the end portion of the bag which is filled with the contents is tightly bound with aluminum wire. The electrodes 5, 5 to be put into close contact with the inspection-object portions 3a, 3a at both ends, which are tightly binding portions, are each made of porous conductive rubber, and recessed portions that can accommodate the inspection-object portions 3a are provided on one side face in central part of the electrodes 5, 5, the recessed portions being formed into a cap-like shape so as to make close contact with the inspection-object portions 3a by being pushed into the portions 3a. The electrodes 5, 5 at both ends are connected to one connecting terminal 5a, and a lead wire 8 is connected to the connecting terminal 5a and then grounded. Thus, by detecting the discharge current that flows through the lead wire 8 when a pinhole is present at the inspection-object portion 3a, with a discharge current detector 7 such as a current transformer (CT), the presence or absence of pinholes in the inspected hermetically sealed package 3 can be detected depending on the presence or absence of the discharge current, as in the foregoing Example 1.

EXAMPLE 4

Figure 4:
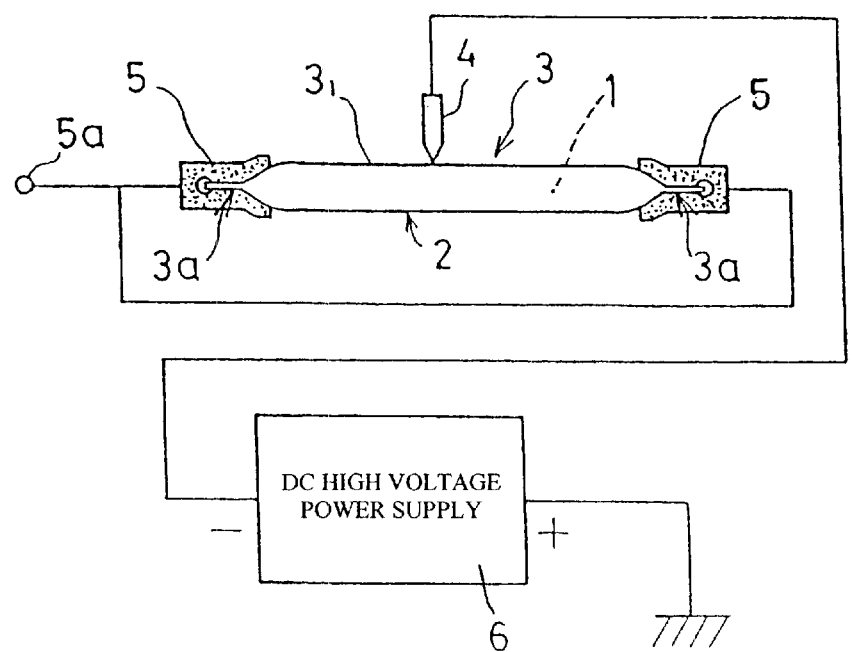
FIG. 4 is an arrangement diagram showing a pre-stage of the inspection method of the invention with a DC high voltage power supply in the case where the hermetically sealed package is food contained in a heat sealed bag such as retort food.

FIG. 4 shows a case where a hermetically sealed package 3, such as retort food (curry, cooked rice, etc.), in which the inspection-object portion 3a is a heat sealed portion of a bag made of plastic film is inspected for the presence or absence of pinholes with a DC high voltage. In such hermetically sealed packages, pinholes which may occur to the electrically insulating film 2 will be concentrated around the inspection-object portions 3a at both ends which are the heat sealed portions.

The electrically conductive contents 1 are completely cooked food contained in a bag. As the electrically insulating film 2, the aforementioned composite plastic film (laminate film) containing no aluminum foil in its inner layer is used.

The electrode 5 to be put into close contact with each inspection-object portion 3*a* is made of porous conductive rubber, and a slit of such a specified shape as to be able to pinch the inspection-object portion 3*a* is provided on one side on the center line. With both sides of the slit opened, the inspection-object portion 3*a* is inserted into the slit so as to be pinched therebetween. The inspection-object end portions 3*a*, 3*a*, which are heat sealed portions on both sides of the hermetically sealed package 3, are pinched by the both-side electrodes 5 in close contact therewith, respectively, where the electrodes 5 are connected to one connecting terminal 5*a*. Then, for the detection of pinholes, as in the foregoing Examples 1 and 3, the single electrical conductor 4 derived from the output terminal of the DC high voltage power supply 6 on the negative side is put into contact with the side face portion $3_1$ of the inspection-object package 3 so that the contents 1 are electrified by a high voltage (0.6 kV–30 kV) of the DC high voltage power supply 6. After that, a lead wire 8 is connected to the connecting terminal 5*a* and then grounded, where a discharge current flowing through the lead wire 8 is detected with the discharge current detector as in the foregoing examples. By this discharge current detection, the presence or absence of any pinholes in the vicinity of the heat sealed portions of the inspection-object hermetically sealed package 3 where pinholes are most likely to occur can be detected.

EXAMPLE 5

Figure 5:
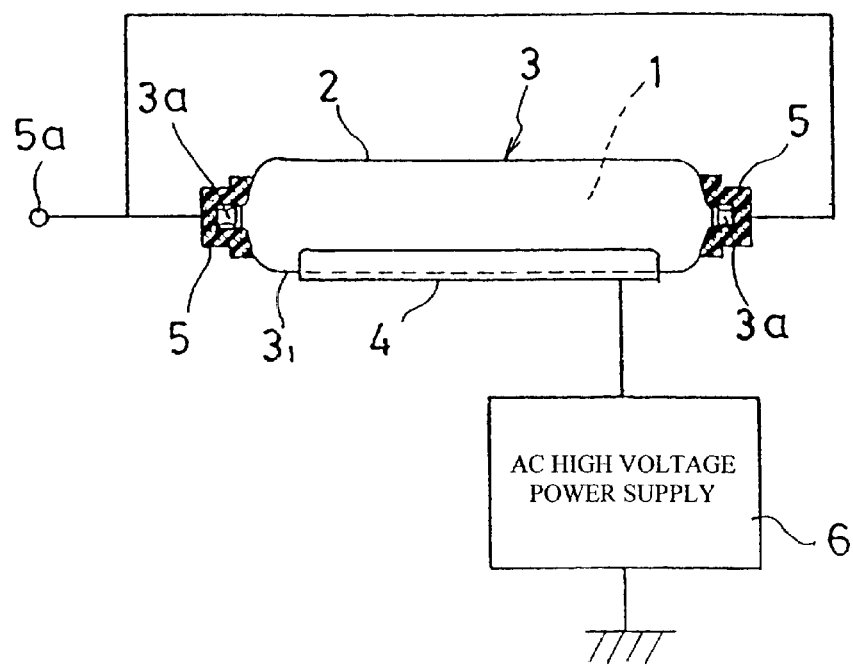
FIG. 5 is an arrangement diagram showing a pre-stage of the inspection method of the invention with an AC high voltage power supply in the case where the hermetically sealed package is a sausage with both ends tightly bound.

FIG. 5 shows a case in which the hermetically sealed package 3 has contents 1 such as fish sausage or the like hermetically sealed with an electrically insulating film 2, with end portions of the contents 1 tightly bound as in Example 3, where the hermetically sealed package 3 is inspected for pinholes with an AC high voltage. In this case, pinholes which may occur to the electrically insulating film 2 will be concentrated around inspection-object portions 3*a*, 3*a* at both ends which are the tightly bound portions of the hermetically sealed bag. The electrodes 5, 5 to be put into close contact with the inspection-object portions 3*a*, 3*a* at both ends, which are tightly binding portions, are cap-like ones made of porous conductive rubber, and put into use by being pushed into the inspection-object portions 3*a*, as in Example 3. The both-end electrodes 5, 5 pushed into the both-end inspection-object portions 3*a*, 3*a*, respectively, are connected to one connecting terminal 5*a*. As the electrode 4 to be put into contact with the side face portion 3, of the hermetically sealed package 3, is used a single support electrode 4 having a circular-arc inner surface so that the cross section of the support electrode 4 corresponds to the circular sausage or the like so as to allow the side face portion $3_1$ to be placed in contact on the support electrode 4. A lower portion of the support electrode 4 is connected via the lead wire to a high-voltage output side terminal of the AC high voltage power supply 6 with output-side one end grounded.

When the hermetically sealed package 3 in which the contents 1 such as fish sausage or the like are hermetically sealed is placed on the support electrode 4 having a circular-arc inner surface, the contents 1 are electrified positively (+) and negatively (−) alternately through the electrically insulating film 2 by varying high potential of the AC high voltage (e.g., 5 kV AC) applied to the support electrode 4.

After that, a lead wire 8 is connected to the connecting terminal 5*a* so as to be grounded, and a discharge current flowing through the lead wire 8 is detected with a discharge current detector 7 as in the foregoing Example. By this discharge current detection, any pinholes in the vicinity of the binding portion of the inspection-object hermetically sealed package 3 where pinholes are most likely to occur can be detected.

EXAMPLE 6

Figure 6:
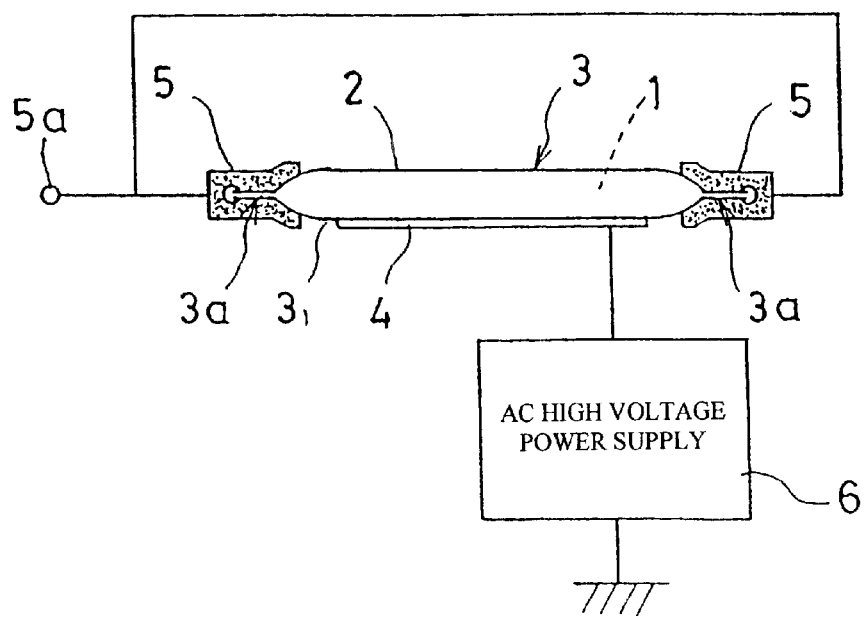
FIG. 6 is an arrangement diagram of the inspection method of the invention with an AC high voltage power supply in the case where the hermetically sealed package is food contained in a heat sealed bag such as retort food.

FIG. 6 shows a case where the hermetically sealed package 3 is a retort food in which the contents 1 such as curry or cooked rice are hermetically sealed with a plastic film 2 with both ends heat sealed as in Example 4, and where the hermetically sealed package 3 is inspected for any pinhole with respect to vicinities of inspection-object portions 3*a*, 3*a* which are heat sealed portions at both ends where pinholes would be concentrated.

The electrodes 5, 5 to be put into close contact with the both-end inspection-object portions 3*a*, 3*a*, which are heat sealed portions, are made of porous conductive rubber, and a slit of such a specified shape as to be able to pinch the inspection-object portion 3*a* is provided on one side on the center line, as in Example 4. With both sides of the slit opened, the inspection-object portion 3*a* is inserted into the slit so as to be pinched therebetween. The electrodes 5, 5 by which the inspection-object portions 3*a*, 3*a* are pinched in close contact, respectively, are connected to one connecting terminal 5*a*. The support electrode 4 for placing thereon the hermetically sealed package 3, which is a retort food, has a flat shape corresponding to the size of the side face portion $3_1$ of the retort food, and a lower portion of the support electrode 4 is connected via the lead wire to a high-voltage output side terminal of the AC high voltage power supply 6 with output-side one end grounded, as in the foregoing Example 5.

When the hermetically sealed package 3, which is a retort food, is placed on the flat-shaped support electrode 4, the retort-food contents 1 are electrified positively (+) and negatively (−) alternately through the plastic film 2 by varying high potential of the AC high voltage applied to the support electrode 4. After that, a lead wire 8 is connected to the connecting terminal 5*a* and then grounded, and a discharge current flowing through the lead wire 8 is detected with a discharge current detector as in the foregoing Example 2.

By this discharge current detection, the presence or absence of pinholes in the vicinity of the heat sealed portions of the retort food 3, which is the inspection-object hermetically sealed package, where pinholes are most likely to occur can be detected.

As described above, in the process of electrifying the contents of the inspection-object hermetically sealed package and performing the inspection by detecting a resultant discharge current, because the discharge current cannot be detected without the presence of pinholes at the inspection-object portion, any pinholes can be detected without errors independently of the atmosphere during the inspection.

In the above examples, in the process of electrifying the contents of the inspection-object hermetically sealed package 3 by using the electrical conductor 4 as an electrode derived from a terminal with a voltage output of the DC high voltage power supply 6, the electrical conductor is connected to the negative (−) side of the DC high voltage power supply whose positive (+) side is grounded. However, it is needless to say that the electrical conductor 4 may also be connected to the positive (+) side of the DC high voltage power supply whose negative (−) side is grounded, by which the contents are electrified.

Furthermore, in addition to the aforementioned examples, the method for inspecting hermetically sealed packages according to the present invention can be applied to injection solutions or ampoules of internal medicine in a similar manner. For example, with the main body portion of an ampoule placed on a support member having a circular-arc inner surface, an electrical conductor derived from a DC high voltage power supply is put into contact with or proximity to a side face of the ampoule, and the content solution within the ampoule is electrified either positively (+) or negatively (−), or otherwise with the support member used as a support electrode having a circular-arc inner surface, an AC high voltage derived from a high-voltage output terminal of an AC high voltage power supply is applied to the support electrode so that the contents are electrified positively (+) and negatively (−) alternately. After that, an electrode is overlaid on an end portion of the ampoule including a neck portion where pinholes are liable to occur. Then, the lead wire derived from the electrode is electrified, where a discharge current from the ampoule flowing through the lead wire is detected, by which an inspection for any pinholes can be achieved.

In the above examples, a lead wire is connected to the connecting terminal of the electrode that has been put into close contact with the inspection-object portion, and the lead wire is grounded, where the pinhole inspection of the inspection-object portion is carried out by detecting a discharge current flowing through the lead wire. However, it is also possible that, depending on the high voltage used, an end portion of the grounded lead wire is put into proximity to the connecting terminal of the electrode that is in close contact with the inspection-object portion, where a pinhole of the inspection-object portion is detected by detecting a discharge current. Like this, various changes may be made without departing from the gist of the invention.

According to the method for inspecting hermetically sealed packages as described in Claim 1 of the present invention, in the pinhole inspection of a hermetically sealed package in which contents such as electrically conductive fluid or powder or food are covered with an electrically conductive film, the contents of the inspection-object hermetically sealed package are electrified with an extremely simple means of using a single electrode derived from a voltage output terminal of the high voltage power supply and putting this electrode into contact with or proximity to a side face portion of the hermetically sealed package, where any pinhole in the inspection-object portion is detected by detecting a discharge current from the contents only when a pinhole is present. With this arrangement, the hermetically sealed package can be inspected for the presence or absence of pinholes effectively with simple means, in combination with the inspection of the inspection-object portion at a site where pinholes are most likely to occur, while fully preventing the occurrence of any misoperations, and without being affected by the atmosphere during the inspection such as humidity or floating fine dusts, as would conventionally be involved in the pinhole detection by the magnitude of the current flowing through the inspection object with the use of a pair of electrodes and with a high voltage applied thereto.

According to the invention as described in claim 2, with a DC high voltage power supply used as the high voltage power supply, an electrical conductor is used as the electrode for electrifying the contents of the hermetically sealed package and can be put into contact with or proximity to a side face portion of the hermetically sealed package. Therefor, the contents of the hermetically sealed package can be electrified with an extremely simple construction and with high easiness and operability.

According to the invention as described in Claim 3, with an AC high voltage power supply used as the high voltage power supply, a support electrode is used as the electrode for electrifying the contents of the hermetically sealed package, by which a discharge current derived from the contents that are electrified positively and negatively alternately can be detected with stability. Still, it never occurs that discharging becomes difficult even if the inspection is repeated, so that the need for an expensive rectifier device for converting the high-voltage AC current into DC current is eliminated, allowing the product to be offered inexpensively.

According to the invention as described in Claim 4, when the inspection-object portion 3a of the hermetically sealed package where pinholes are most likely to occur is constant in shape because of mass production, the electrode made of electrically conductive rubber or electrically conductive plastic is put into close contact with the inspection-object portion by using its elasticity so that the hermetically sealed package can be easily inspected.

What is claimed is:

1. A method for inspecting, for any pinhole, a hermetically sealed package 3 which contents 1 selected from the group consisting of electrically conductive fluid or powder or food are covered by and are in contact with an electrically insulating film 2, the method comprising the ordered steps of: putting a single first electrode 4 connected to a voltage output terminal of a high voltage power supply 6 into contact with said electrically insulating film 2 of a side face portion 3₁ of the hermetically sealed package 3; electrifying the contents 1 in the hermetically sealed package 3 using said single first electrode 4 then placing a second electrode 5 into close contact with or opposed proximity to an inspection-object portion 3a of the hermetically sealed package 3; then grounding said second electrode 5; and detecting a discharge current from the inspection-object portion 3a to thereby detect any pinhole of the hermetically sealed package 3 when said second electrode 5 is grounded.

2. The method for inspecting a hermetically sealed package according to claim 1, wherein the high voltage power supply 6 is a DC high voltage power supply and the electrode 4 derived from the voltage output terminal of the high voltage power supply 6 is an electrical conductor.

3. The method for inspecting a hermetically sealed package according to claim 1, wherein the high voltage power supply 6 is an AC high voltage power supply and the electrode 4 derived from the voltage output terminal of the high voltage power supply 6 is a support electrode for the side face portion 3₁ of the hermetically sealed package 3.

4. The method for inspecting a hermetically sealed package according to claim 1 or 2 or 3, wherein the electrode 5 is electrically conductive rubber or electrically conductive plastic which is formed so as to be closely contactable with the inspection-object portion 3a.

5. The method for inspecting according to claim 2, wherein the high voltage source is a 0.6 to 30 KV source.

6. The method according to claim 3, wherein the high voltage source is a 0.6 to 30 KV source.

7. The method according to claim 2, further comprising the step of moving the single first electrode 4 out of contact with the hermetically sealed package 3 before placing said second electrode 5 in contact with or close proximity to said hermetically sealed package 3.

8. The method according to claim 5, further comprising the step of moving the single first electrode 4 out of contact with the hermetically sealed package 3 before placing said second electrode 5 in contact with or close proximity to said hermetically sealed package 3.

9. The method according to claim 2, wherein said second electrode 5 comprises two separate electrodes and each of said two separate electrodes is put into close contact with or opposed proximity to opposite ends of said hermetically sealed package 3.

10. The method according to claim 3, wherein said second electrode 5 comprises two separate electrodes and each of said two separate electrodes is put into close contact with or opposed proximity to opposite ends of said hermetically sealed package 3.

11. The method according to claim 6, wherein said second electrode 5 comprises two separate electrodes and each of said two separate electrodes is put into close contact with or opposed proximity to opposite ends of said hermetically sealed package 3.

* * * * *

UNITED STATES PATENT AND TRADEMARK OFFICE
CERTIFICATE OF CORRECTION

PATENT NO.     : 6,634,216 B1
DATED          : October 21, 2003
INVENTOR(S)    : Kenji Yasumoto It is certified that error appears in the above-identified patent and that said Letters Patent is hereby corrected as shown below:

Title page,
Item [54], Title, change "INSPECTION METHOD FOR SEALED PACKAGE" to
-- METHOD FOR INSPECTING HERMETICALLY SEALED PACKAGES --

Signed and Sealed this

Twenty-sixth Day of July, 2005

JON W. DUDAS
*Director of the United States Patent and Trademark Office*